(12) United States Patent
Lathrop et al.

(10) Patent No.: US 11,185,285 B2
(45) Date of Patent: Nov. 30, 2021

(54) SYSTEMS AND METHODS FOR INTEGRATING ELECTRONICS INTO A MOUTH GUARD

(71) Applicant: INTEL CORPORATION, Santa Clara, CA (US)

(72) Inventors: Braxton Lathrop, Lake Oswego, OR (US); Cody Gabriel, Beaverton, OR (US); James Hall, Woodstock, CT (US); Michael Rosen, San Jose, CA (US); Nathan Stebor, Portland, OR (US); Philip Muse, Folsom, CA (US); Rita Brugarolas Brufau, Hillsboro, OR (US); Shea Dillon, Beaverton, OR (US); Stephanie Moyerman, Phoenix, AZ (US); Steven Xing, San Francisco, CA (US); Tyler Fetters, Hillsboro, OR (US)

(73) Assignee: INTEL CORPORATION, Santa Clara, CA (US)

( * ) Notice: Subject to any disclaimer, the term of this patent is extended or adjusted under 35 U.S.C. 154(b) by 223 days.

(21) Appl. No.: 16/232,292

(22) Filed: Dec. 26, 2018

(65) Prior Publication Data

US 2019/0125261 A1 May 2, 2019

(51) Int. Cl.
*A61B 5/02* (2006.01)
*A61B 5/00* (2006.01)
(Continued)

(52) U.S. Cl.
CPC ............ *A61B 5/682* (2013.01); *A61B 5/0028* (2013.01); *A61B 5/02416* (2013.01);
(Continued)

(58) Field of Classification Search
CPC ... A61B 5/682; A61B 5/02416; A61B 5/0028; A61B 5/02438; A61B 5/14551; A61B 2560/0214; A61B 2503/10; A61B 2560/0219; A61B 2562/164; A61B 2562/166; A61B 5/14552; A63B 71/085; A63B 2220/40; A63B 2220/803; A63B 2209/00; A63B 2071/0625; A63B 2220/833; A63B 2220/51; A63B 2230/08; A63B 2071/065; A63B 2071/0694; A63B 2071/0655; A63B 2220/80; A63B 2230/207; A63B 2225/20; A63B 2209/02; A63B 2071/0663; A63B 71/0622;
(Continued)

(56) References Cited

U.S. PATENT DOCUMENTS

| | | | | |
|---|---|---|---|---|
| 6,089,864 A | * | 7/2000 | Buckner | .................... A61F 5/56 433/6 |
| 2008/0064993 A1 | * | 3/2008 | Abolfathi | ............. H04R 25/606 601/47 |

(Continued)

*Primary Examiner* — Amanda K Hulbert
*Assistant Examiner* — Natasha Patel
(74) *Attorney, Agent, or Firm* — Fletcher Yoder, P.C.

(57) ABSTRACT

Mouth guard that includes a flexible printed circuit board encapsulated within a base member is provided. The flexible printed circuit board includes multiple separate stiff sections spaced apart from each other within the base member. One or more electronic devices are disposed within the base member. In particular, the one or more electronics are disposed on the base member.

15 Claims, 8 Drawing Sheets

(51) Int. Cl.
*A63B 71/08* (2006.01)
*H01M 8/16* (2006.01)
*H01M 16/00* (2006.01)
*H04R 1/02* (2006.01)
*H04R 1/46* (2006.01)
*A61B 5/024* (2006.01)
*H02J 7/34* (2006.01)
*A61B 5/1455* (2006.01)

(52) U.S. Cl.
CPC ........ *A61B 5/02438* (2013.01); *A63B 71/085* (2013.01); *H01M 8/16* (2013.01); *H01M 16/003* (2013.01); *H04R 1/028* (2013.01); *H04R 1/46* (2013.01); *A61B 5/14551* (2013.01); *A61B 5/14552* (2013.01); *A61B 2503/10* (2013.01); *A61B 2560/0214* (2013.01); *A61B 2560/0219* (2013.01); *A61B 2562/164* (2013.01); *A61B 2562/166* (2013.01); *A63B 2220/40* (2013.01); *H01M 2250/30* (2013.01); *H02J 7/345* (2013.01)

(58) Field of Classification Search
CPC .......... A63B 2220/805; A63B 2230/00; A63B 2071/0627; A63B 2225/50; A63B 2071/0661; A63B 2071/0666; A63B 2071/063; A63B 2220/53; A63B 2230/06; A63B 2220/30; H01M 8/16; H01M 16/003; H01M 2250/30; Y02E 60/50; Y02B 90/10; H02J 2310/23; H02J 2300/30; H02J 2207/50; H02J 50/10; H02J 50/005; H02J 7/00; H02J 7/345; H04R 2420/07; H04R 2460/13; H04R 1/028; H04R 1/46
See application file for complete search history.

(56) References Cited

U.S. PATENT DOCUMENTS

| | | | |
|---|---|---|---|
| 2013/0040264 A1* | 2/2013 | Scurtescu | A61C 7/00 433/119 |
| 2013/0211270 A1* | 8/2013 | Laurent | A61B 5/4875 600/508 |
| 2014/0187875 A1* | 7/2014 | Paris | A61B 5/682 600/301 |
| 2015/0119759 A1* | 4/2015 | Gonzales | A63B 71/085 600/595 |
| 2015/0173856 A1* | 6/2015 | Lowe | A61C 7/00 433/24 |
| 2016/0338626 A1* | 11/2016 | Wang | A61B 5/14507 |
| 2020/0147473 A1* | 5/2020 | Maloney | B29C 51/266 |

* cited by examiner

SYSTEMS AND METHODS FOR INTEGRATING ELECTRONICS INTO A MOUTH GUARD

BACKGROUND

The present disclosure relates generally to the integration of electronics into a mouth guard.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

The scientific and medical research related to head trauma, in particular with regards to sports related concussions, has been increasing. To further this research, it is desirable to collect and analyze measurement data of the traumatic events. One such technique for providing this data may include sensing traumatic events utilizing a mouth guard to generate more accurate models of what the athlete experiences during a traumatic event. For example, biosensing systems may be utilized with the mouth guard to collect the data. However, these mouth guards incorporating the biosensing systems tend to be inflexible, uncomfortable, and cumbersome due to size of the electronics and/or the how the electronics are incorporated with the mouth guard, which discourages the user from wearing the mouth guard.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
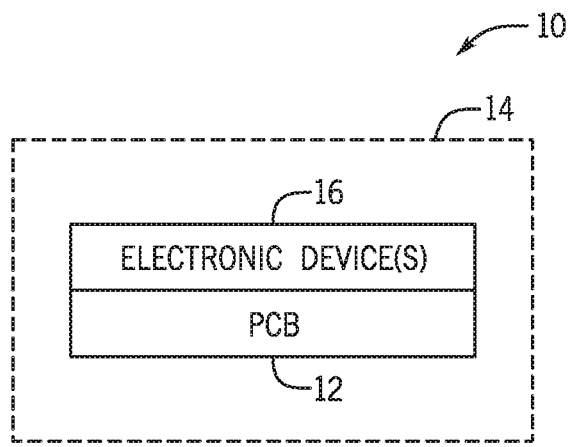
FIG. 1 is a block diagram of a mouth guard having a flexible printed circuit board (PCB), in accordance with an embodiment of the present disclosure.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed in further detail below, embodiments of the present disclosure relate generally to providing a mouth guard that includes one or more electronic devices integrated within the mouth guard in a manner that makes the mouth guard less cumbersome and more comfortable for the user to wear. More specifically, the present disclosure relates to utilizing a flexible printed circuit board (PCB) that utilizes a plurality of separate stiff sections that are interconnected. The flexible PCB may be integrated in a front portion (e.g., labial-buccal portion) of the mouth guard. Each stiff section may include multiple layers such as a stiffener layer (e.g., closest to the user's teeth) and alternating layers of polyamide and adhesive layers.

The one or more electronic devices may be disposed on one or more of the stiff sections of the flexible PCB. In certain embodiments, the electronic devices may include one or more energy harvesting microbial fuel cells to generate and store power from the saliva within the user's mouth. The harvesting microbial fuel cells may solely or supplement power provided to other electronic devices within the mouth guard. In certain embodiments, the electronic devices disposed on the stiff sections of the flexible PCB of the mouth guard may be utilized to monitor a physiological parameter of the user. For example, the electronic devices may include a heart rate monitor disposed within a location of the mouth guard adjacent an artery in the face to measure the heart rate of the user. In certain embodiments, the electronic devices disposed on the stiff sections of the flexible PCB of the mouth guard may be utilized to facilitate communication between the user (e.g., athlete) and another person (e.g., coach). For example, the electronic devices may include a bone conducting device (e.g., bone conducting speaker) disposed within the mouth guard that can remotely receive communications from a transmitter (e.g., associated with another person such as the coach) and communicates them via the user's teeth and skull to the user's ear. These and other electronic devices may be integrated in the mouth guard on the flexible PCB to provide a less cumbersome and more comfortable mouth guard for the user.

With the foregoing in mind, FIG. 1 illustrates a block diagram of a mouth guard 10 that may include the flexible PCB 12. The mouth guard 10 may include the flexible PCB 12 encapsulated within a base member 14. For example, the mouth guard 10 may be molded around the flexible PCB 12 with the separate but interconnected stiff sections spaced apart (e.g., laterally) from each other along base member 14. The flexible PCB 12 may minimize the bulkiness of the mouth guard 10 while also increasing the comfort of it for the user. One or more electronic devices 16 may be integrated on one or more of the stiff sections of the flexible PCB 12. Although the electronic devices 16 below are described as integrated on the flexible PCB 12, in certain embodiments, the electronic devices 16 may be integrated within the mouth guard 10 without the flexible PCB 12.

The electronic devices 16 may include one or more devices for harvesting energy. For example, one or more energy harvesting microbial fuel cells (MFCs) may be disposed on the flexible PCB 12 within the base member 14. As described in greater detail below, the MFCs utilize the saliva of the user to generate power. One or more MFCs may be coupled to an energy harvesting circuit. Although the energy harvesting MFCs are described in detail below, other energy harvesting mechanisms may be utilized. For example, a piezoelectric device may be utilized to use the mechanical energy generated in the user's mouth (e.g., due to movement) to generate power. The energy harvesting devices may be utilized to solely or supplement power provided to one or more of the other electronic devices 16 within the base member 14.

The electronic devices 16 may include devices for monitoring one or more physiological parameters of the user (e.g., athlete). For example, a photoplethysmograph (PPG) heart rate monitoring device may be utilized to measure the heart rate of the user. In some embodiments, the heart rate monitoring device may be disposed within the mouth guard 10 at a location adjacent an artery in the face and/or gums for measurements. If multiple wavelengths are utilized by the heart rate monitoring device other physiological parameters may be monitored via pulse oximetry such as peripheral capillary oxygen saturation ($SpO_2$). Although the heart rate monitoring device is described in detail below, other devices may be utilized to determine physiological parameters of the user. For example, accelerometers may be utilized to measure the speed of the user and/or concussive forces experienced by the user.

The electronic devices 16 may include a device to enable discrete communication with the user of the mouth guard 10 from a person and location separate from the user (e.g., coach on sideline and/or in a booth). The device may include a bone conducting device (e.g., bone conducting speaker) that may receive communications from a transmitter associated with another person (e.g., coach) and transmit the communication to the user (e.g., athlete) via the user's teeth and skull. The bone conducting device is completely encapsulated within the base member 14 to make it waterproof and keeps the user from directly contacting the components of the bone conducing device. In certain embodiments, the bone conducting device may be able to communicate with other electronic devices in the mouth guard 10. For example, the heart rate monitoring device may communicate with the bone conducting device to communicate an alarm related to an abnormal physiological parameter (e.g., irregular heart beat).

Each electronic device 16 may be associated with one or more different components such as controllers (having memory devices and processors), wireless communication devices (Bluetooth, ultra-wide band, etc.), wireless charging devices, energy storage devices (capacitors, etc.). Additionally or alternatively, the mouth guard 10 may have these different components integrated within the base member 14 separate from the electronic devices 16. For example, additional energy storage devices may be integrated within the mouth guard 10 to provide power to the different electronic devices 16. In some embodiments, the memory of the electronic devices 16 may include one or more tangible, non-transitory, computer-readable media that store instructions executable by a processor and/or data to be processed by the processor. For example, the memory may include random access memory (RAM), read only memory (ROM), rewritable non-volatile memory such as flash memory, hard drives, optical discs, and/or the like. Additionally, the processor of the electronic devices 16 may include one or more general purpose microprocessors, one or more application specific processors (ASICs), one or more field programmable logic arrays (FPGAs), or any combination thereof.

Figure 2:
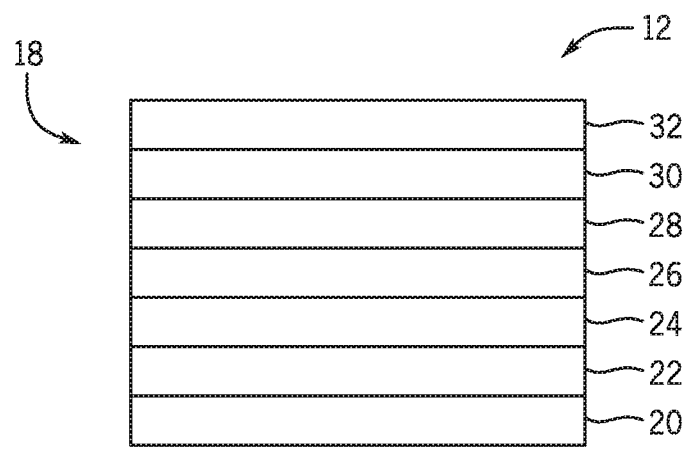
FIG. 2 is a schematic diagram of a section of a flexible PCB, in accordance with an embodiment of the present disclosure.

Turning now to a more detailed discussion of the flexible PCB 12, FIG. 2 illustrates a schematic diagram of a stiff section 18 of the flexible PCB 12. As noted above, each stiff section 18 of the flexible PCB 12 includes a plurality of layers. The layer closest to the user's teeth (bottom-most layer) within the mouth guard 10 may be a stiffener layer 20. The stiffener layer 20 may be composed of a glass-reinforced epoxy laminate material. In particular, the stiffener layer 20 may be composed of an FR4 grade material. The stiffener layer 20 may be configured to provide some stiffness or rigidity to the section 18. The remaining layers of the section may include one or more adhesive layers (e.g., layers 22, 26, 30) and one or more polyamide layers (e.g., layers 24, 28, 32). The number of total layers of the section 18 may vary. In addition, the number of each of the layer types (e.g., stiffener, adhesive, and polyamide) may vary. Although FIG. 2 depicts the adhesive and polyamide layers as alternating, these layers may be arranged differently.

Figure 3:
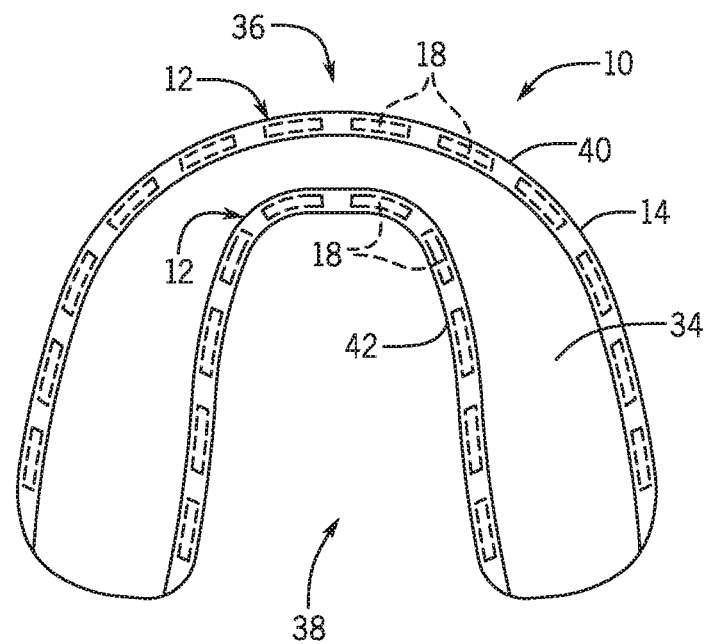
FIG. 3 is a schematic diagram of a top view of a mouth guard having a flexible PCB, in accordance with an embodiment.
Figure 4:
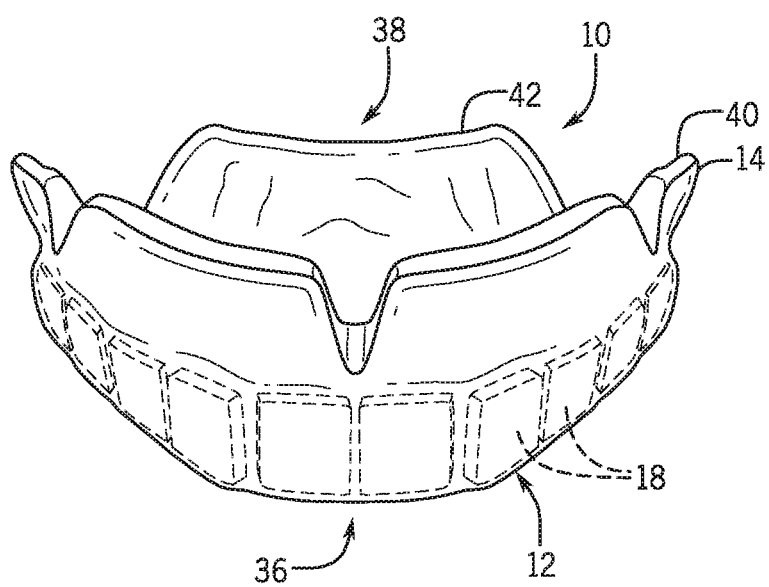
FIG. 4 is a front perspective view of a mouth guard having a flexible PCB, in accordance with an embodiment.

FIG. 3 provides a schematic top view of the different locations of the flexible PCB 12 of the mouth guard 10. As depicted, the base member 14 of the mouth guard 10 includes a U-shape. The mouth guard 10 may include a biting surface 34 configured, when disposed within the user's mouth, to be positioned between occlusal tooth surfaces of the upper and lower teeth. The base member 14 also may include an anterior portion 36, a posterior portion 38, a labial-buccal side 40 (e.g., front portion), and a lingual side 42 (e.g., rear portion). When the mouth guard 10 is disposed within the user's mouth, the anterior portion 36 faces the opening of the mouth, the posterior portion 38 faces the rear of the mouth (e.g., near the molars), the labial-buccal side 40 faces the user's inner cheeks, and the lingual side 42 faces the user's tongue. The flexible PCB 12 may be fully encapsulated within the base member 14. In a preferred embodiment, the flexible PCB 12 may be disposed within the labial-buccal side 40 of the mouth guard 10. For example, FIG. 4 depicts the flexible PCB 12 solely in the labial-buccal side 40 of the mouth guard 10. In particular, the separate stiff sections 18 of the flexible PCB 12 may be disposed adjacent each other (e.g., spaced apart or lateral spaced) along the base member 14. The separate stiff sections 18 may be interconnected via electronic devices 16 disposed on the respective sections 18 and/or electrical connections disposed on the respective sections 18. The number of sections 18 may also vary. Turning back to FIG. 3, in certain embodiments, the flexible PCB 12 may be disposed in the lingual side 42 of the base member 14. In certain embodiments, a respective flexible PCB 12 may be disposed in both the labial-buccal side 40 and the lingual side 42 of the base member 14. The flexible PCB 12 minimizes the bulkiness of the mouth guard 10 and makes the mouth guard 10 more comfortable for the user. Thus, the user may be encouraged to wear the mouth guard 10. In certain embodiments, each separate stiff section may be associated with a respective tooth the user's mouth.

Figure 5:
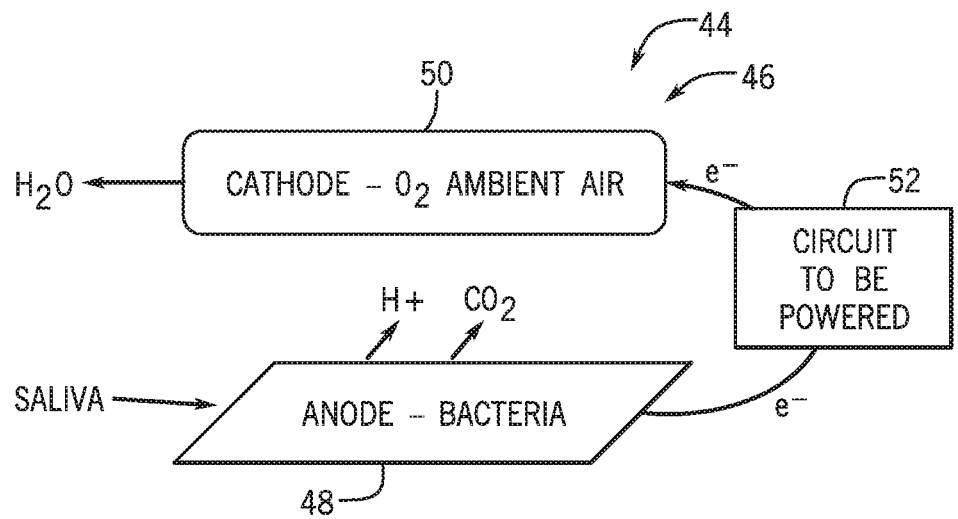
FIG. 5 is a schematic diagram of an equivalent circuit of an energy harvesting microbial fuel cell (MFC), in accordance with an embodiment.
Figure 6:
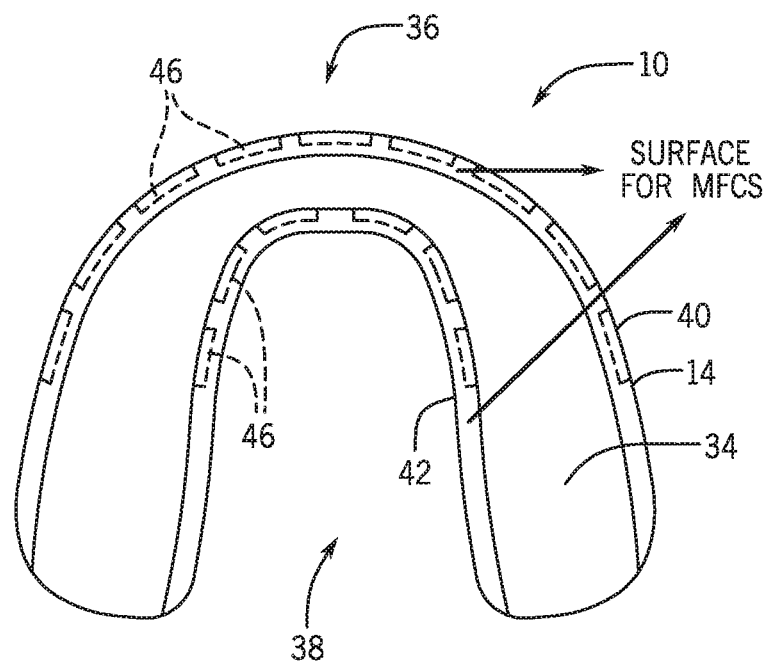
FIG. 6 is a schematic diagram of a top view of a mouth guard illustrating locations for MFCs, in accordance with an embodiment.

As mentioned above, an energy harvesting MFC is one of the electronic devices that may be disposed on the flexible PCB 12 within the mouth guard 10. FIG. 5 is a schematic diagram of an equivalent circuit 44 of the MFC 46. The MFC 46 includes an anode 48 and a cathode 50. The anode 48 of the MFC 46 may not be disposed within mouth guard 10. Instead, the anode 48 may be disposed on the surface of the mouth guard 10 and exposed to the saliva within the user's mouth. The exposed surface area of the anode 48 may vary. In addition, the current densities and load generated by the MFC 46 may also vary. In certain embodiments, a plurality of MFCs 46 embedded on the mouth guard 10 may include a total anode surface area of at least 375 mm$^2$. The number of MFCs 46 embedded on the mouth guard 10 may vary. The anode 48 may be made of graphene that contains bacteria that performs the decomposition of organic fluid (e.g., saliva within the user's mouth). The decomposition of the organic fluid by the bacteria may generate protons, $CO_2$, and electrons. The electrons may be utilized to power a circuit 52 (e.g., energy harvesting circuit). Oxygen within the ambient air may serve as an acceptor (i.e., act as the cathode 50) to generate water. As depicted in FIG. 6, the MFCs 46 may be disposed on the labial-buccal side 40 and/or the lingual side 42 of the base member 14.

Figure 7:
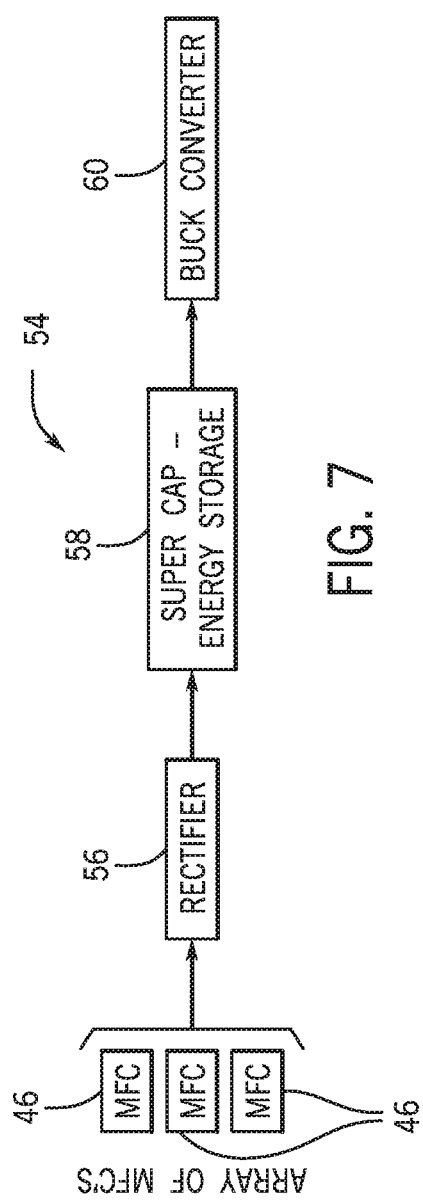
FIG. 7 is a block diagram of an energy harvesting circuit including an array of MFCs, in accordance with an embodiment.

In some embodiments, the output current of the MFCs 46 may not be sufficient to use as a direct power source for circuits (e.g., of other electronic devices within the mouth guard 10). Thus, the energy generated by the MFCs 46 may be harvested. FIG. 7 illustrates a block diagram of an energy harvesting circuit 54 coupled to a plurality of MFCs 46. Although FIG. 7 depicts multiple MFCs 46 coupled to the energy harvesting circuit 54, in certain embodiments, each MFC 46 on the mouth guard 10 may be associated with a respective energy harvesting circuit 54. The energy harvesting circuit 54 may include a rectifier 56, a super capacitor 58, and a buck converter 60 (e.g., step down converter). The output current of the MFCs 46 may be rectified into a direct current (DC) voltage suitable for energy storage in the super capacitor 58. The buck converter 60 (e.g., DC/DC buck converter) may transform the storage voltage to a required output voltage or current for operation of the circuit (e.g., of the other electronic device(s) within the mouth guard 10). The MFCs 46 may solely power and/or supplement power to one or more electronic devices within the mouth guard 10 via the energy harvesting circuit 54.

Figure 8:
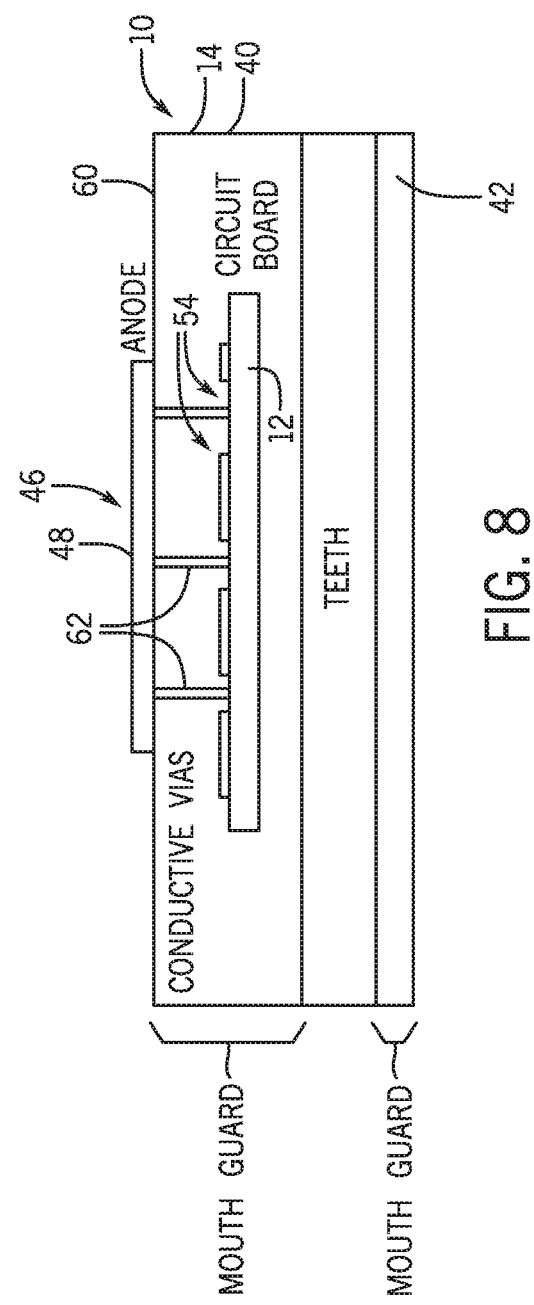
FIG. 8 is a cross-sectional top view of the mouth guard illustrating an interconnection between the MFC and the energy harvesting circuit and the flexible PCB, in accordance with an embodiment.
Figure 9:
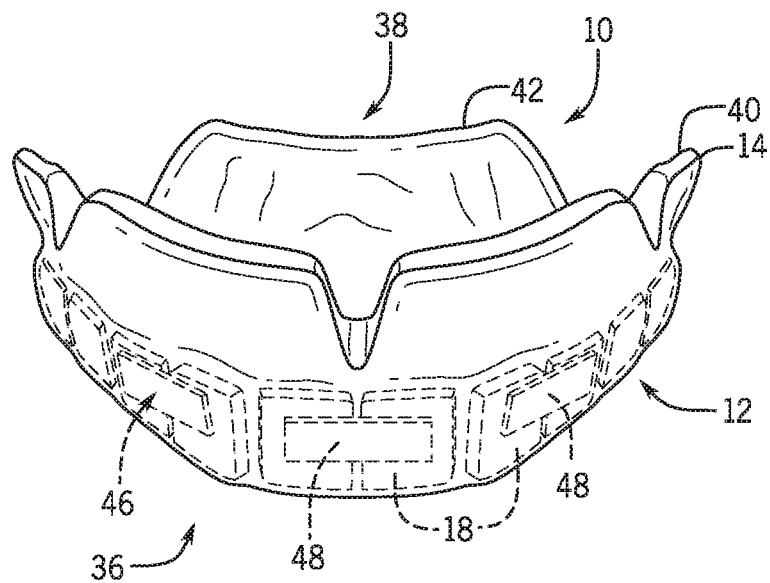
FIG. 9 is a front perspective view of a mouth guard having MFCs disposed on a flexible PCB, in accordance with an embodiment.

While the anode 48 of the MFC 46 may be exposed to the user's saliva, the components of the energy harvesting circuit 54 may be embedded within the base member 14 of the mouth guard 10. FIG. 8 is a cross-sectional top view of the mouth guard 10 illustrating an interconnection between the MFC 46 and the energy harvesting circuit 54 and the flexible PCB 12. As depicted in FIG. 8, the anode 48 of the MFC 46 may be disposed on an outer surface 61 (i.e., facing the user's cheek) of the labial-buccal side 40 of the base member 14. The components (e.g., rectifier 56, super capacitor 58, and buck converter 60) of the energy harvesting circuit 54 may be disposed on the flexible PCB 12 within the labial-buccal side 40 of the base member 14. Conductive vias 62 within the labial-buccal side 40 may couple (e.g., electrically couple) the anode 48 to the energy harvesting circuit 54. The anode 48 of the MFC 46 and/or the components of the energy harvesting circuit 54 may be disposed on multiple laterally adjacent stiff sections 18 of the flexible PCB 12 as depicted in FIG. 9. Also, as depicted in FIG. 9, the mouth guard 10 may include multiple MFCs 46. In certain embodiments, the anode 48 of the MFC 46 and/or the components of the energy harvesting circuit 54 may be disposed on a single stiff section 18 of the flexible PCB 12.

The utilization of the MFCs 46 may help avoid or minimize the utilization of other sources of power (e.g., batteries such as a lithium-ion polymer battery), which may enable the reduction in size of electronic devices disposed within the mouth guard 10 (as well as the size of the mouth guard 10). The MFCs 46 may also provide a source of power with better usability. In particular, the MFCs 46 may provide a source of power without a life limit. In addition, the MFCs 46 may not need to be recharged. Further, the MFCs 46 (in particular, the anodes 48) may not need to be disposed within the mouth guard 10), which enables the MFCs 46 to be replaced when needed without having to replace the entire mouth guard 10, thus, providing a more simple and cost effective option.

Figure 10:
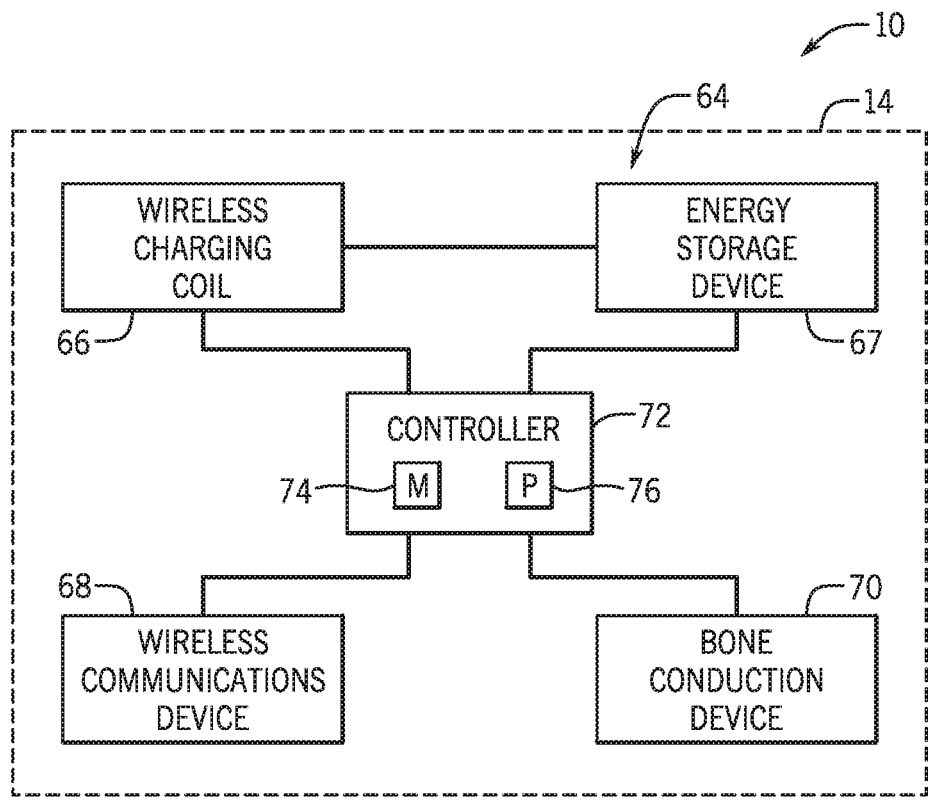
FIG. 10 is a block diagram of a bone conducting device disposed within a mouth guard, in accordance with an embodiment.

As mentioned above, a bone conducting device may be disposed on the flexible PCB 12 within the mouth guard 10. FIG. 10 is a block diagram of a bone conducting device 64 (e.g., bone conducting speaker). The bone conducting device 64 may be completely encapsulated within the mouth guard 10, which makes the device 64 waterproof and protects the user from contacting the device 64. In addition, the bone conducting device 64 may maintain a fixed position with respect to the user's teeth.

The bone conducting device 64 may include a wireless charging coil 66 to provide power to the device 64 (e.g., via inductive charging). Power provided by the wireless charging coil 66 may be stored in an energy storage device 67 (e.g., battery such as a lithium-ion polymer battery). In certain embodiments, the bone conducting device 64 may be powered (or partially powered) from energy collected by the MFCs 46 discussed above. The bone conducting device 64 may also include a wireless communications device or interface 68 to enable communications between the bone conducting device 64 and a transmitter or transceiver remote from the user of the mouth guard 10 (e.g., associated with a communication device of another person). The wireless communications device 68 may include a wireless transceiver or receiver. The wireless communications device 68 may utilize any suitable wireless communication protocol, such as an ultra-wideband (UWB) communication standard, a Bluetooth communication standard, or any 802.11 communication standard. The communication range between the bone conducting device 64 and the remote transmitter or transceiver may range from 30 meters to several meters.

The bone conducting device 64 may further include a bone conduction device 70. The bone conduction device 70 may include a piezoelectric vibration device or a metal rod in a voice coil driven by an oscillating current. The wireless charging coil 66, the energy storage device 67, the wireless communications device 68, and the bone conduction device 70 may be coupled to a controller 72 that controls the operation of the bond conducting device or speaker 64. The controller 72 may include a memory 74 and a processor 76 as described above. The controller 72 may receive the wireless communication signal transmitted from the remote transmitter (via the wireless communications device 68) and then drives the bone conduction device 70 to vibrate. The vibrations (e.g., sound waves) may be conducted through the teeth and skull to the inner ear of the user where the vibrations are translated into sound that only the user of the mouth guard 10 can hear. Thus, the mouth guard 10 with the bone conducting device 64 forms a discrete communications device that may be utilized in a number of situations (e.g., sporting events, military operations, etc.). Unlike current communications technology which involves multiple separate components, the mouth guard 10 with the bone conduction device 70 may provide a single platform that acts as a stand-alone discrete auditory communications device. In certain embodiments, the bone conducting device 64 may be utilized to communicate information from other electronic devices within the mouth guard 10 to the user (e.g., without the use of the wireless communications device 68). For example, in certain embodiments, a warning or alarm of an abnormal condition related to a physiological parameter (e.g., abnormal heart beat) detected by a heart rate monitoring device within the mouth guard 10 may be communicated via the bone conducting device 64. For example, a sound or verbal communication may be communicated via the bone conducting device 64.

Figure 11:
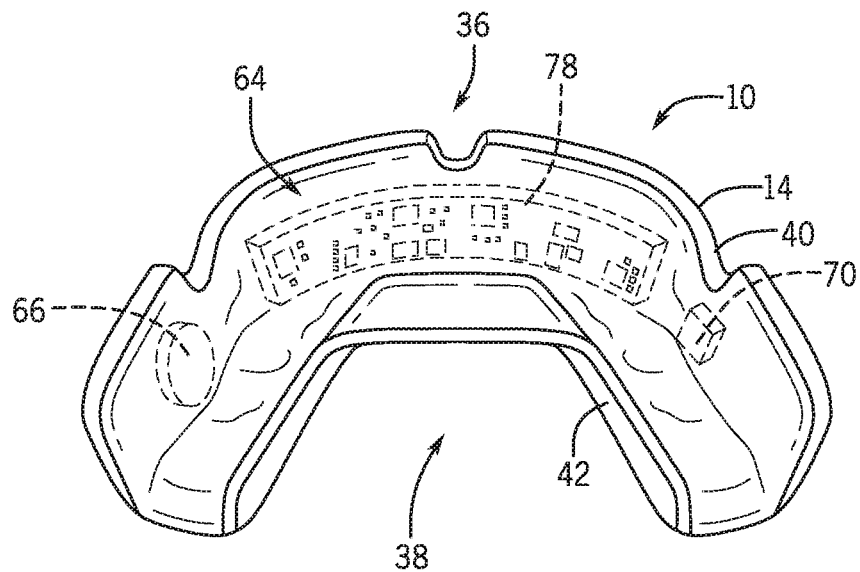
FIG. 11 is a rear perspective view of a mouth guard having a bone conducting device, in accordance with an embodiment.

FIG. 11 is a rear perspective view of the mouth guard 10 having a bone conducting device 64. As depicted in FIG. 11, the bone conducting device 64 may be encapsulated within the base member 14 of the mouth guard 10 without the flexible PCB 12. The wireless charging coil 66 and the bone conduction device 70 are disposed in the left and right sides of the labial-buccal side 40 of base member 14, while other components 78 (e.g., controller 72, wireless communications device 68, etc.) are centrally disposed within the labial-buccal side 40 of the base member 14. In certain embodiments, the bone conducting device or speaker 64 may be disposed in the lingual side 42 of the base member 14. As depicted, the mouth guard 10 has been press fit for the maximum comfort and protection of the user. In particular, the mouth guard 10 may be fitted to make a tight connection with the molars. For example, as noted above, the right side of the base member 14 has the bone conduction device 70 that has a tight fit with the molars to conduct sound.

Figure 12:
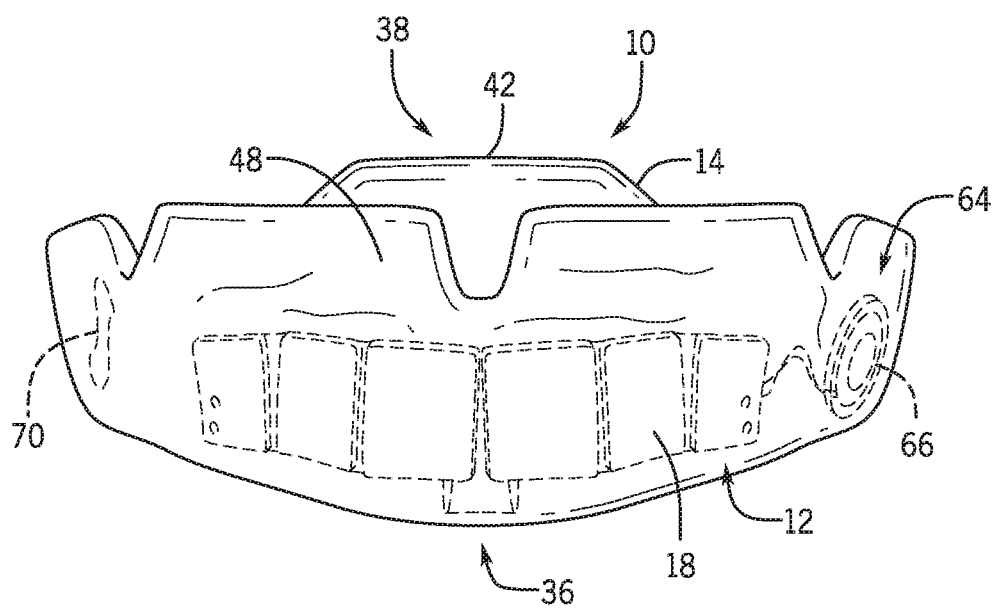
FIG. 12 is a front perspective view of a mouth guard having a bone conducting device disposed on a flexible PCB; in accordance with an embodiment.

In certain embodiments, the bone conducting device 64 is disposed on the flexible PCB 12 within the mouth guard 10 as depicted in FIG. 12. As depicted in FIG. 12, components of the bone conducting device 64 may be disposed on the multiple stiff sections 18 of the flexible PCB along the mouth guard 10. For example, as depicted in FIG. 12, the wireless charging coil 66 and the bone conducting device 70 are disposed on separate stiff sections 18 of the flexible PCB 12.

Figure 13:
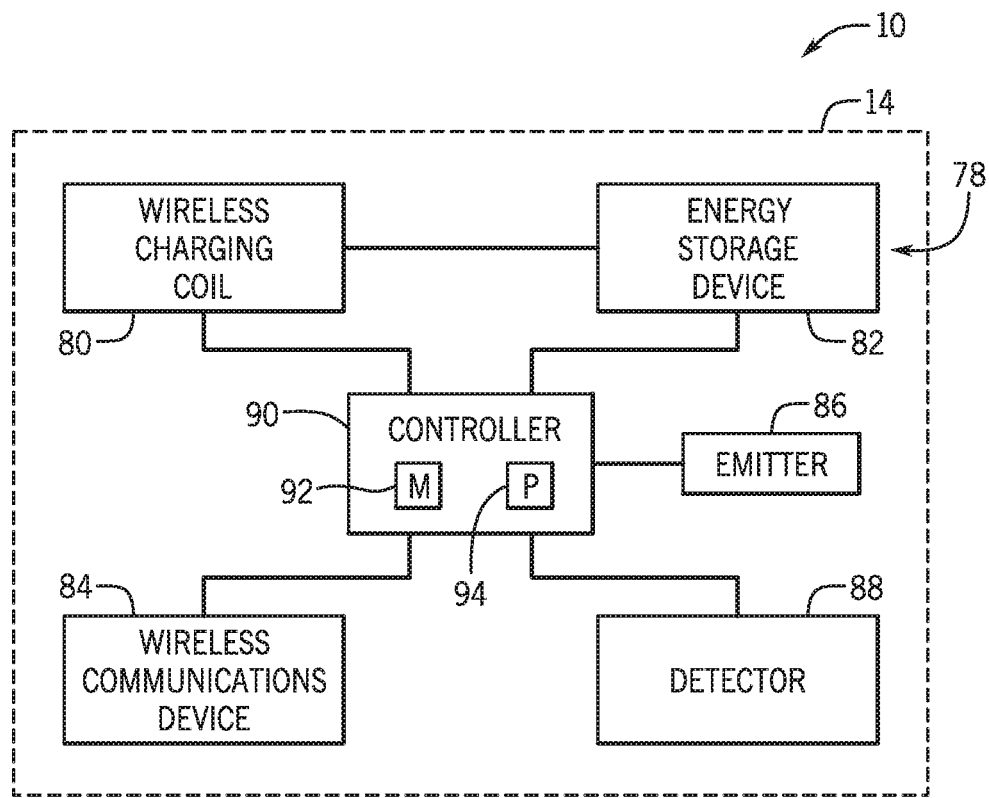
FIG. 13 is a block diagram of a heart rate monitoring device disposed within a mouth guard, in accordance with an embodiment.

As mentioned above, a heart rate monitoring device may be disposed on the flexible PCB 12 within the mouth guard 10. FIG. 13 is a block diagram of a heart rate monitoring device 78 disposed within the mouth guard 10. The heart rate monitoring device 78 may be completely encapsulated within the mouth guard 10. In particular, each component of the heart rate monitoring device 78 may be disposed on one or more stiff sections 18 of the flexible PCB 12. In certain embodiments, the components of the heart rate monitoring device 78 may be disposed within the mouth guard 10 without the flexible PCB 12. In certain embodiments, the mouth guard 10 may include a single heart rate monitoring device 78. In other embodiments, the mouth guard 10 may include more than one heart rate monitoring device 78 (e.g., 2, 3, 4 or more devices 78). The heart rate monitoring device 78 is configured to be located within the base member 14 of the mouth guard 10 adjacent an arterial location within the user's face and/or gums to enable the device 78 to acquire a plethysmographic signal at one or more wavelengths to determine one or more physiological parameters of the user.

The heart rate monitoring device 78 may include a wireless charging coil 80 to provide power to the device 78 (e.g., via inductive charging). Power provided by the wireless charging coil 78 may be stored in an energy storage device 82 (e.g., battery such as a lithium-ion polymer battery). In certain embodiments, the bone heart rate monitoring device 78 may be powered (or partially powered) from energy collected by the MFCs 46 discussed above. The heart rate monitoring device 78 may also include a wireless communications device or interface 84 to transmit physiological data to a remote location. The wireless communications device 80 may include a wireless transceiver. The wireless communications device 80 may utilize any suitable wireless communication protocol, such as an ultra-wideband (UWB) communication standard, a Bluetooth communication standard, or any 802.11 communication standard.

The heart rate monitoring device 78 may also include an emitter 86 and a detector 88. Light from the emitter 86 (e.g., at one or more certain wavelengths) may pass into the user of the mouth guard 10 where the portions of the light may be differentially scattered, absorbed, and/or transmitted. Light that emerges from the user's tissue within the mouth may be detected by the detector 88. In certain embodiments, the emitter 86 may emit light from one or more LEDs or other suitable light sources into a pulsatile tissue. The reflected or transmitted light may be detected with the detector 88, such as photodiode or photo-detector, after the light has passed through or has been reflected by the pulsatile tissue. In certain embodiments, a plethysmographic signal at a single wavelength may be obtained that enables a determination of a heart rate of the user of the mouth guard 10. In certain embodiments, a plethysmographic signal may be obtained at at least a couple of wavelengths (e.g., red and infrared) to determine the $SpO_2$ and/or heart rate of the user of the mouth guard 10. The wireless charging coil 80, the energy storage device 82, the wireless communications device 84, the emitter 86, and the detector 88 may be coupled to a controller 90 that controls the operation of the heart rate monitoring device 78. The controller 90 may include a memory 92 and a processor 94 as described above. The controller 90 may control the emission of light from the emitter and receive the detected signals from the detector 88. In certain embodiments, the controller 90 may partially process the detected signals and transmit (via the wireless communications device 84) the processed signals to a remote location where the one or more physiological parameters may be detected. In certain embodiments, the controller 90 may fully process the detected signals to determine the one or more physiological parameters and then transmit (via the wireless communications device 84) the physiological parameters to a remote location. In certain embodiments, the data collected by the heart rate monitoring device 78 may be stored within the memory 92 for later transmission when requested or at a fixed interval. In certain embodiments, the data collected by the heart rate monitoring device 78 may be continuously transmitted (via the wireless communications device 84) to a remote location. In certain embodiments, the memory 92 may store one or more ranges or thresholds. The heart rate monitoring device 78 may compare one or more physiological parameters to these ranges or thresholds and provide a warning or alarm signal if the one or more physiological parameters are abnormal or approaching abnormal (e.g., irregular heart beat). In certain embodiments, the warning or alarm signal may be provided to the bone conducting device described above disposed within the mouth guard 10 to provide an audio warning or alarm to the user of the mouth guard 10. In certain embodiments, the one or more physiological parameters and/or associated alarms or warnings may be displayed on a screen of a device worn by the user of the mouth guard 10. For example, a football player may wear a helmet that includes a visor configured to display the physiological parameters and/or associated alarms. In certain embodiments, a soldier may wear a wrist watch configured to display the physiological parameters and/or associated alarms.

Figure 14:
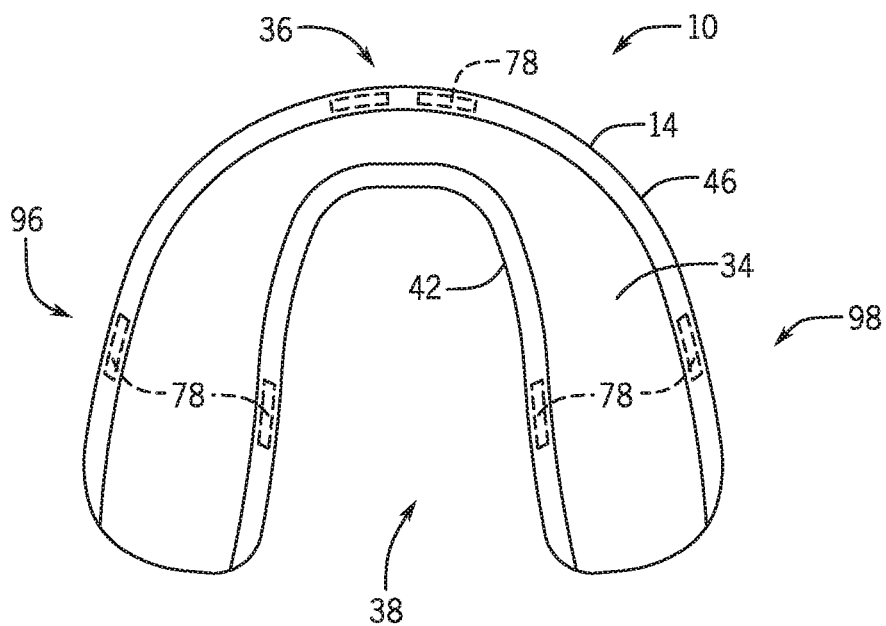
FIG. 14 is a schematic diagram of a top view of a mouth guard illustrating locations for a heart rate monitoring device, in accordance with an embodiment.
Figure 15:
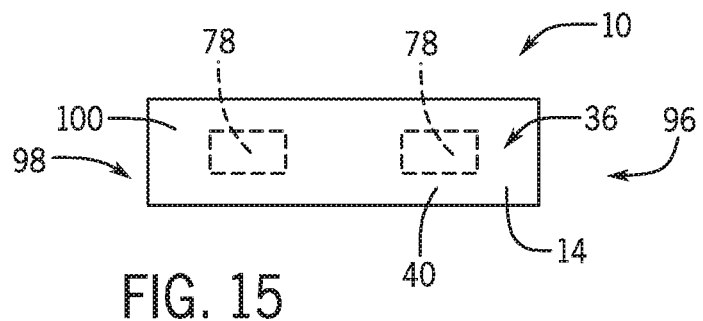
FIG. 15 is a schematic diagram of a front view of a mouth guard that extends in front of a user's upper teeth illustrating locations for a heart rate monitoring device, in accordance with an embodiment.
Figure 16:
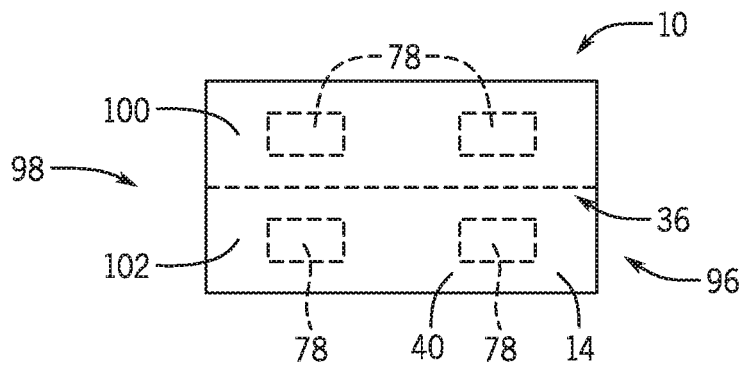
FIG. 16 is a schematic diagram of a front view of a mouth guard that extends in front of a user's upper and lower teeth illustrating locations for a heart rate monitoring device, in accordance with an embodiment.

The heart rate monitoring device 78 may be disposed at a variety of locations within the mouth guard 10. In particular, the heart rate monitoring device 78 may be located within the mouth guard 10 at a location adjacent an artery in the user's mouth and/or gums to facilitate the acquisition of the physiological data. For example, the heart rate monitoring device 78 may be located adjacent the septal artery, the inferior labial artery, or the superior labial artery. FIGS. 14-16 illustrate the various locations within the mouth guard 10 where the heart rate monitoring device 78 may be located. As depicted in FIG. 14, the heart rate monitoring device 78 may be located in the labial-buccal side 40 and/or the lingual side 42 of the base member 14. In addition, the heart rate monitoring device 78 may be located in the anterior portion 36 and/or the posterior portion 38 of the base member 14. Further, the heart rate monitoring device 78 may be located on the left side 96 or the right side 98 of the base member 14. In certain embodiments, as depicted in FIG. 15, the mouth guard 10 may only include an upper portion 100 that extends across the user's upper teeth. Thus, the heart rate monitoring device 78 may be disposed in the upper portion 100 and only acquire physiological data from arterials locations of the user's mouth or gums adjacent the upper teeth. In certain embodiments, as depicted in FIG. 16, the base member 14 may include both the upper portion 100 that extend across the user's upper teeth and a lower portion 102 that extends across the user's lower teeth. The heart rate monitoring device in the mouth guard 10 in FIG. 16 may be located in the upper portion 100 and/or the lower portion 102 of the base member 14. Thus, the heart rate monitoring device 78 may acquire physiological data from arterials locations of the user's mouth or gums adjacent the upper teeth and/or lower teeth.

Figure 17:
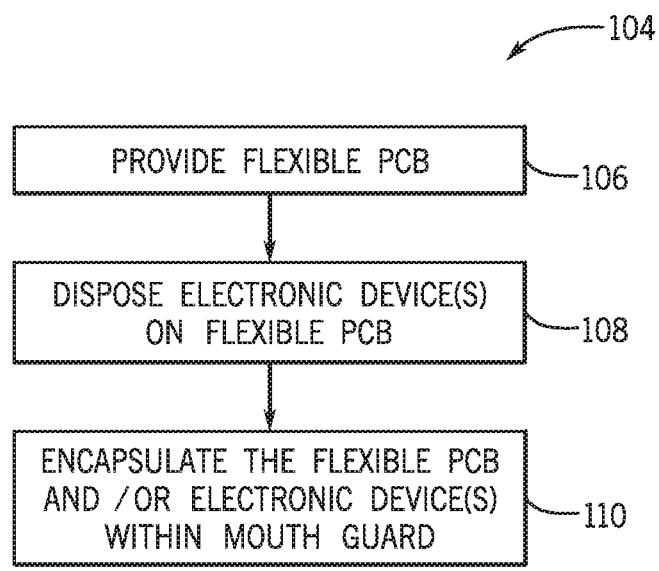
FIG. 17 is a process flow diagram of a method for manufacturing a mouth guard having a flexible printed circuit board (PCB), in accordance with an embodiment.

FIG. 17 is a process flow diagram of a method 104 for manufacturing the mouth guard having the flexible PCB 12. The method 104 may include providing the flexible PCB 12 that includes the separate stiff sections 18 (block 106). The flexible PCB 12 as described above. The method 104 may also include disposing on or coupling to the flexible PCB 12 one or more electronic devices 16 (block 108). The electronic devices 16 may include accelerometers, heart rate monitoring devices, bone conducting devices or speakers, energy harvesting MFCs, and/or other electronic devices. The method 104 may further include encapsulating the flexible PCB 12 and/or the one or more electronic devices 16 within the base member of the mouth guard 10 (block 110). For example, the mouth guard 10 may be molded or fabricated about the flexible PCB 12 and/or the one or more electronic devices 16 utilizing the typical techniques for fabricating the mouth guard 10. Depending on the type of mouth guard 10, the flexible PCB 12 and/or the one or more electronic devices 16 may be disposed in an upper portion of the mouth guard that extends over the user's upper teeth or a lower portion of the mouth guard that extends over the user's lower teeth or both the upper and lower portions. In certain embodiments, the flexible PCB 12 and/or the one or more electronic devices 16 may be disposed in the labial-buccal side, the lingual side, and/or both the labial-buccal and lingual sides. Certain electronic devices 16 may not be encapsulated within the mouth guard 10. For example, the anode of the MFC may be disposed on an outer surface of the mouth guard 10.

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. Accordingly, the disclosure is to cover all modifications, equivalents, and alternatives falling within the spirit and scope of the disclosure as defined by the following appended claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

What is claimed is:

1. A mouth guard, comprising:
a base member configured to fit inside a mouth of a user; and
at least one electronic device disposed within the base member, wherein at least one electronic device is disposed on a flexible printed circuit board encapsulated within base member, and wherein the flexible printed circuit board comprises a plurality of separate stiff sections laterally spaced apart from each other within the base member, and the plurality of separate stiff sections are physically and directly interconnected within the base member via the at least one electronic device, additional electronic devices, or electrical connections disposed on the plurality of separate stiff sections;
wherein the base member comprises a labial-buccal portion configured to be disposed in front of the user's teeth and a lingual portion configured to be disposed behind the user's teeth, and the flexible printed circuit board is encapsulated within the labial-buccal portion, wherein the at least one electronic device comprises at least one energy harvesting microbial fuel cell configured to power another electronic device, and wherein the at least one energy harvesting microbial fuel cell is coupled to an energy harvesting circuit comprising a rectifier, a supercapacitor, and a buck converter.

2. The mouth guard of claim 1, wherein each separate stiff section of the plurality of separate stiff sections comprises a plurality of layers.

3. The mouth guard of claim 2, wherein the plurality of layers comprises a stiffener layer closest to the user's teeth.

4. The mouth guard of claim 3, wherein the stiffener layer comprises a glass-reinforced epoxy laminate material.

5. The mouth guard of claim 3, wherein the plurality of layers comprises one or more polyamide layers and one or more adhesive layers disposed on the stiffener layer.

6. The mouth guard of claim 1, wherein the at least one electronic device comprises a bone conducting device configured to receive a remote communication and to conduct the communication to the user's ear via the user's teeth and skull.

7. The mouth guard of claim 1, wherein the at least one electronic device comprises a heart rate monitoring device.

8. The mouth guard of claim 7, wherein the heart rate monitoring device is disposed within the base member at a location configured to be adjacent an artery of the user's face.

9. The mouth guard of claim 1, wherein the at least one energy harvesting microbial fuel cell comprises an anode disposed outside the base member, while a remainder of the microbial fuel cell is disposed within the base member.

10. The mouth guard of claim 1, wherein the plurality of separate stiff sections are physically and directly interconnected within the base member in a serial manner.

11. A mouth guard, comprising:
a base member configured to fit inside a mouth of a user;
a bone conducting device disposed within the base member and configured to receive a remote audible communication and to conduct the remote audible communication to the user's ear via the user's teeth and skull;
an energy harvesting microbial fuel cell disposed within the base member and configured to power the bone conducting device, wherein energy harvesting microbial fuel cell is coupled to an energy harvesting circuit comprising a rectifier, a supercapacitor, and a buck converter; and
a flexible printed circuit board encapsulated within a labial-buccal portion of the base member, wherein the flexible printed circuit board comprises a plurality of separate stiff sections disposed along the labial-buccal portion, and wherein components of the bone conducting device and the energy harvesting microbial fuel cell are both disposed on the plurality of stiff sections within the base member and directly and physically interconnect at least some stiff sections of the plurality of stiff sections within the base member.

12. The mouth guard of claim 11, wherein each separate stiff section of the plurality of separate stiff sections comprises a plurality of layers.

13. The mouth guard of claim 12, wherein the plurality of layers comprises a stiffener layer closest to the user's teeth, and wherein the plurality of layers comprises one or more polyamide layers and one or more adhesive layers disposed on the stiffener layer.

14. A mouth guard, comprising:
a base member configured to fit inside a mouth of a user; and
at least one energy harvesting microbial fuel cell disposed within the base member and configured to power another electronic device within the base member, wherein the at least one energy harvesting microbial fuel cell comprises an anode disposed outside the base member, while a remainder of the microbial fuel cell is disposed within the base member.

15. The mouth guard of claim 14, comprising a flexible printed circuit board encapsulated within a labial-buccal portion of the base member, wherein the flexible printed circuit board comprises a plurality of separate stiff sections disposed within the labial-buccal portion laterally spaced apart from each other, and wherein remainder of the microbial fuel cell is disposed on the plurality of stiff sections within the base member and directly and physically interconnect at least some stiff sections of the plurality of stiff sections within the base member.

* * * * *